United States Patent
Lor

(10) Patent No.: US 10,280,017 B2
(45) Date of Patent: May 7, 2019

(54) TRANSPORTATION SYSTEM FOR PARAFFIN EMBEDDED TISSUES

(71) Applicant: Kuo-Lung Lor, New Taipei (TW)

(72) Inventor: Kuo-Lung Lor, New Taipei (TW)

( * ) Notice: Subject to any disclaimer, the term of this patent is extended or adjusted under 35 U.S.C. 154(b) by 193 days.

(21) Appl. No.: 15/437,041

(22) Filed: Feb. 20, 2017

(65) Prior Publication Data

US 2018/0127220 A1    May 10, 2018

(30) Foreign Application Priority Data

Nov. 10, 2016   (TW) .............................. 105217181 U

(51) Int. Cl.
  *G01N 35/04*   (2006.01)
  *B65G 65/00*   (2006.01)
  *G01N 1/36*    (2006.01)

(52) U.S. Cl.
  CPC ............ *B65G 65/00* (2013.01); *G01N 35/04* (2013.01); *G01N 1/36* (2013.01); *G01N 2035/042* (2013.01); *G01N 2035/0422* (2013.01); *G01N 2035/0425* (2013.01); *G01N 2035/0441* (2013.01)

(58) Field of Classification Search
  CPC .......... B65G 37/004; G01N 2035/042; G01N 2035/0425; B25J 15/0047
  USPC .......................... 414/223.01, 331.02, 331.05
  See application file for complete search history.

(56) References Cited

U.S. PATENT DOCUMENTS

| | | | | |
|---|---|---|---|---|
| 5,019,927 A | * | 5/1991 | Simone ................ | G11B 15/688 360/92.1 |
| 5,607,275 A | * | 3/1997 | Woodruff ............. | G11B 15/688 360/92.1 |
| 5,999,356 A | * | 12/1999 | Dimitri ................ | G11B 15/688 360/71 |
| 6,385,003 B1 | * | 5/2002 | Ellis .................... | G11B 15/6825 360/92.1 |
| 6,848,876 B2 | * | 2/2005 | Babbs .................... | B65G 1/045 414/217.1 |
| 7,622,079 B2 | * | 11/2009 | Lehto ................... | G01N 35/109 422/510 |
| 7,918,639 B2 | * | 4/2011 | Fink ....................... | B25J 9/041 414/266 |
| 2008/0286086 A1 | * | 11/2008 | Fink ....................... | B25J 9/041 414/787 |
| 2010/0278627 A1 | * | 11/2010 | Williamson, IV ...... | B01L 3/508 414/800 |

* cited by examiner

*Primary Examiner* — Mark C Hageman
(74) *Attorney, Agent, or Firm* — Li & Cai Intellectual Property (USA) Office

(57) ABSTRACT

A transportation system for paraffin embedded tissues includes a placing assembly, a bearing unit and a storage device. The placing assembly includes a horizontal moving assembly, a vertical moving assembly, a rotation assembly and a placing unit. The horizontal and vertical moving assemblies move the placing unit in horizontal and vertical directions, respectively, and the rotation assembly allows the placing unit to rotate around a vertical axis. The bearing unit receives the paraffin embedded tissues. The storage device has a rotation plate including a plurality of receiving slots each for storing the bearing unit. The placing unit is configured to remove the bearing unit from the storage device, move the bearing unit to a processing apparatus located at another side of the placing assembly, remove the bearing unit from the processing apparatus, and transport the bearing unit to the receiving slot of the storage device.

9 Claims, 15 Drawing Sheets

TRANSPORTATION SYSTEM FOR PARAFFIN EMBEDDED TISSUES

BACKGROUND

1. Technical Field

The instant disclosure relates to a transportation system, in particular, to a transportation system for paraffin embedded tissues.

2. Description of Related Art

Conventional paraffin embedded tissues such as the paraffin embedded tissues for tissue array are operated and transported manually. Therefore, operation and transportation of a large amount of paraffin embedded tissue cannot be effectively conducted. Although some companies have developed semi-automatic operation equipment for paraffin embedded tissues to significantly reduce the time for operating a large amount of paraffin embedded tissues, such techniques are still unable to solve the problem of the transportation of a large amount of paraffin embedded tissues. The transportation of a large amount of paraffin embedded tissues is still conducted manually.

SUMMARY

The main object of the instant disclosure is to provide a transportation system for paraffin embedded tissues for solving the problem mentioned above.

In order to achieve the above object, an embodiment of the instant disclosure provides a transporting system for paraffin embedded tissues, comprising a placing assembly, a bearing unit and a storage device. The placing assembly comprises a horizontal moving assembly, a vertical moving assembly, a rotation assembly and a placing unit. The placing unit is connected to the horizontal moving assembly, and the horizontal moving assembly is connected to the vertical moving assembly and the rotation assembly. The horizontal moving assembly and the vertical assembly are configured to move the placing unit in horizontal and vertical directions, and the rotation assembly is configured to rotate the placing unit around a vertical axis. The bearing unit is for receiving the paraffin embedded tissues. The storage device is disposed at a side of the placing assembly and has a rotation plate. The rotation plate has a plurality of receiving slots for storing the bearing unit. The placing unit is configured to remove the bearing unit from the storage device and move the bearing unit to a processing apparatus located at another side of the placing assembly. The placing unit is configured to remove the bearing unit from the processing apparatus and transport the bearing unit to one of the receiving slots of the storage device.

The bearing unit has a bearing slot, a limiting slot and a limiting structure, the bearing slot being configured to receive the paraffin embedded tissues. The placing unit has a positioning component. The horizontal moving assembly is configured to place the placing unit into the limiting slot and remove the placing unit from the limiting slot for engaging the positioning component with the limiting structure of the limiting slot and separating the positioning component from the limiting structure of the limiting slot respectively. When the positioning component and the limiting structure are engaged with each other, the horizontal moving assembly separates the placing unit and the bearing unit from the receiving slot.

The placing unit has a body. The positioning component comprises two first positioning members and a first elastic member, the two first positioning members and the first elastic member being disposed on the body, the first elastic member being disposed between the two first positioning members, and the two first positioning members each having a portion corresponding to two walls opposite to each other and exposed from the body. A compressed distance of the first elastic member when the positioning component and the limiting structure engage with each other is less than a compressed distance of the first elastic member when the positioning component and the limiting structure do not engage with each other.

The positioning component further comprises a second positioning member disposed on the body, the second positioning member being configured to move the two first positioning members away from the body when the first elastic member is compressed. The placing unit is controlled by the horizontal moving assembly and separates from the limiting slot when the second positioning member limits the movement of the two first positioning members.

The second positioning member has an engaging portion. The body and the two first positioning members are configured to move relative to the second positioning member, and the limiting slot of each bearing unit has the positioning unit disposed therein. The engaging portion of the second positioning member is configured to engage with the positioning unit of each bearing unit. When the placing unit is inserted in the limiting slot and the engaging portion of the second positioning member engages with the positioning unit, the body and the two first positioning members are controlled by the horizontal moving assembly and move relative to the second positioning member, and the two first positioning members separate from the second positioning member and engage with the limiting structure.

The second positioning member has an engaging slot at an end adjacent to the two first positioning members, the engaging slot being configured to receive the two first positioning members and to limit the two first positioning members from moving away from the body. When the placing unit is inserted in the limiting slot and the two first positioning members and the limiting structure engage with each other, the placing unit is configured to be controlled by the horizontal moving assembly to move toward the limiting slot for guiding the two first positioning members moving toward each other by the limiting structure, such that the two first positioning members are received in the engaging slot.

The placing unit further comprises a second elastic member disposed on the body, with an end of the second elastic member being fixed on the body, and the other end of the elastic member abutting the second positioning member. When the two first positioning members are received in the engaging slot, the second elastic member is compressed and allows a portion of the second positioning member to abut a portion of each of the two first positioning members.

The placing assembly further comprises a buffering unit having an end connected to the horizontal moving assembly, and the other end connected to the body. The body is configured to swing upwardly or downwardly relative to the buffering unit within a predetermined range.

The storage device comprises a plurality of rotation plates stacked on each other and spaced apart from each other, and the rotation plates are configured to rotate around a same axis.

The transportation system comprises a plurality of storage devices each comprising a plurality of rotation plates stacked on each other and spaced apart from each other, and the rotation plates are controlled to rotate around a same axis. The storage devices are configured to be controlled and rotate or move relative to each other.

The advantages of the instant disclosure reside in that the transportation system for paraffin embedded tissues can significantly increase the transportation speed of a large amount of paraffin embedded tissues.

In order to further understand the techniques, means and effects of the instant disclosure, the following detailed descriptions and appended drawings are hereby referred to, such that, and through which, the purposes, features and aspects of the instant disclosure can be thoroughly and concretely appreciated; however, the appended drawings are merely provided for reference and illustration, without any intention to be used for limiting the instant disclosure.

BRIEF DESCRIPTION OF THE DRAWINGS

The accompanying drawings are included to provide a further understanding of the instant disclosure, and are incorporated in and constitute a part of this specification. The drawings illustrate exemplary embodiments of the instant disclosure and, together with the description, serve to explain the principles of the instant disclosure.

DESCRIPTION OF THE EXEMPLARY EMBODIMENTS

Figure 1:
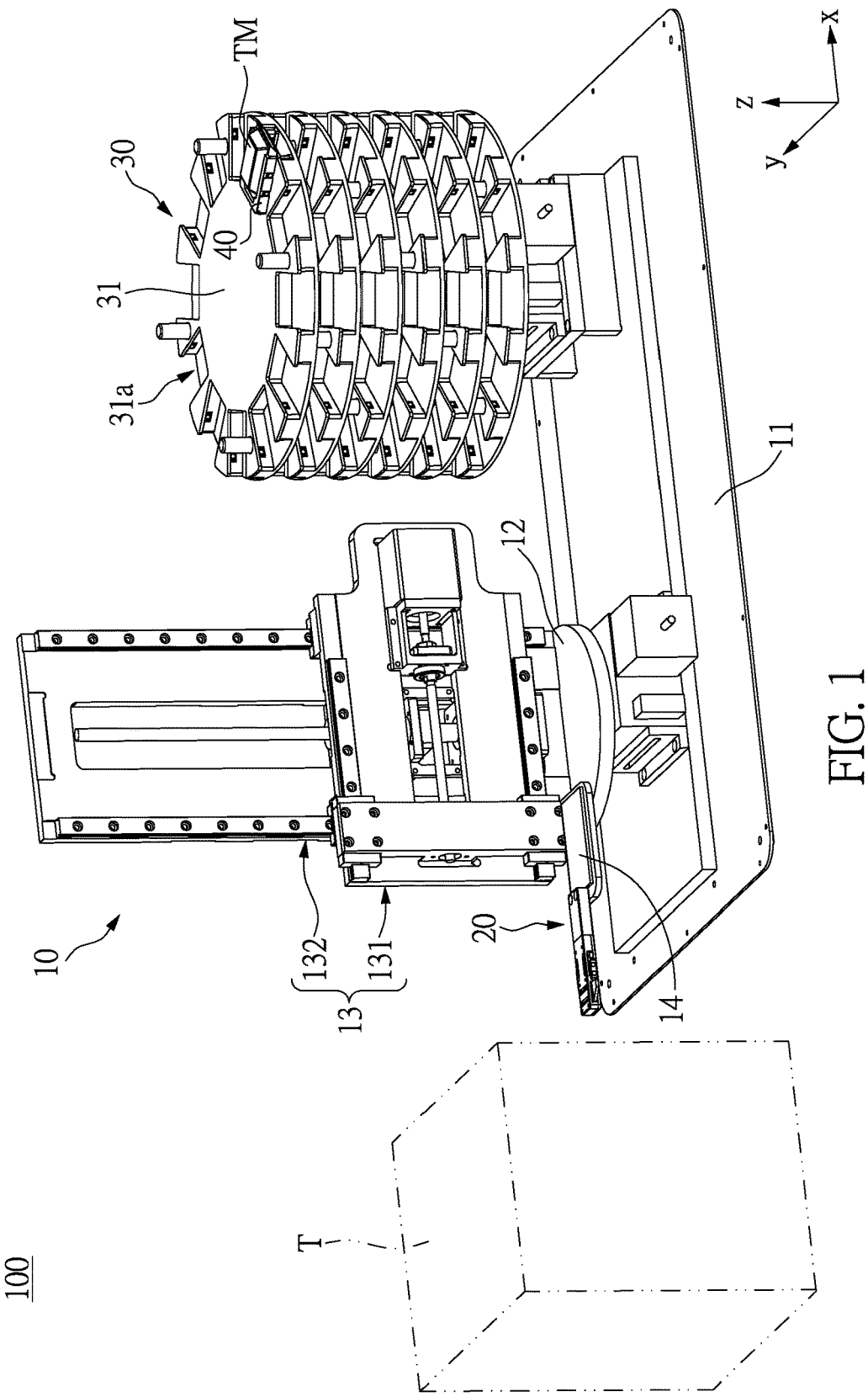
FIG. 1 and FIG. 2 are schematic diagrams of a transportation system for paraffin embedded tissues of the instant disclosure.

Reference will now be made in detail to the exemplary embodiments of the instant disclosure, examples of which are illustrated in the accompanying drawings. Wherever possible, the same reference numbers are used in the drawings and the description to refer to the same or like parts.

Figure 2:
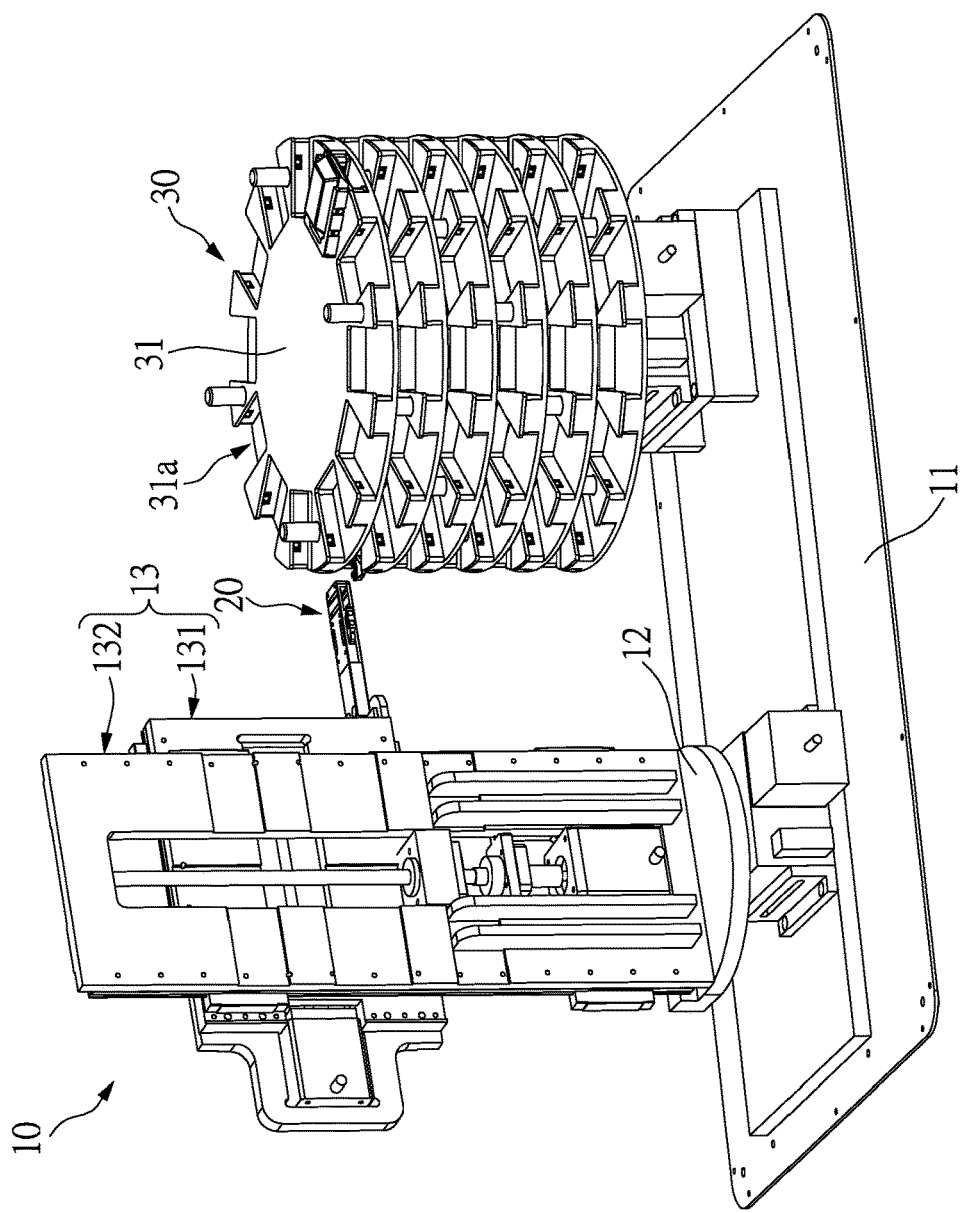

FIG. 1 and FIG. 2 are schematic diagrams of the transportation system for paraffin embedded tissues of the instant disclosure. Referring to FIG. 1 and FIG. 2, the transportation system for paraffin embedded tissues 100 includes a placing assembly 10, a storage device 30 and a bearing unit 40. The placing assembly 10 includes a fixing base 11, a rotation assembly 12, a moving assembly 13, a connecting unit 14 and a placing unit 20. The placing unit 20 can be driven by the rotation assembly 12 and the moving assembly 13 to move horizontally, vertically or to rotate for moving the bearing unit 40 and a paraffin embedded tissues TM thereon from a processing apparatus T at a side of the placing assembly 10 to the storage device 30 located at another side of the placing assembly 10.

In addition, the rotation assembly 12 and the moving assembly 13 are fixed on the fixing base 11. The connecting unit 14 is connected to the moving assembly 13, and the connecting unit 14 is connected to the placing unit 20. The rotation assembly 12 can allow the connecting unit 14 to rotate relative to the fixing base 11. The moving assembly 13 can allow the connecting unit 14 to move relative to the fixing base 11, thereby driving the placing unit 20 to move between the processing apparatus T and the storage device 30. Therefore, the transportation of the bearing unit 40 and the paraffin embedded tissues TM thereon between the processing apparatus T and the storage device 30 can be achieved.

In practice, the moving assembly 13 includes a horizontal moving assembly 131 and a vertical moving assembly 132. The horizontal moving assembly 131 is connected to the placing unit 20 through the connecting unit 14, and the horizontal moving assembly 131 allows the connecting unit 14 to move horizontally (along the X axis shown in the figures). The vertical moving assembly 132 is connected to the horizontal moving assembly 131 and the rotation assembly 12 and allows the placing unit 20 to move vertically (along the Z axis shown in the figures). The rotation assembly 12 allows the placing unit 20 to rotate around the vertical axis (the Z axis).

The horizontal moving assembly 131 and the vertical moving assembly 132 can be linear rails. However, the instant disclosure is not limited thereto. In the figures of the present embodiment, the rotation assembly 12 is connected to the vertical moving assembly 132, the horizontal moving assembly 131 is connected to the vertical moving assembly 132, and the horizontal moving assembly 131 is connected to the placing unit 20 through the connecting unit 14. However, the above connection manner is only an example, and the instant disclosure is not limited thereto. The connection manner of the components can be adjusted based on actual needs.

The storage device 30 comprises a plurality of rotation plates 31. The rotation plates 31 are stacked on each other and spaced apart from each other. The rotation plates 31 can be controlled to rotate around a same axis. In actual implementation, the rotation plates 31 can rotate together or individually. In other embodiments, the storage device 30 can have only one single rotation plate 31. The rotation plates 31 each has a plurality of receiving slots 31a spaced apart from each other. The receiving slots 31 are used to receive the bearing unit 40 and the paraffin embedded tissues TM thereon.

Figure 3:
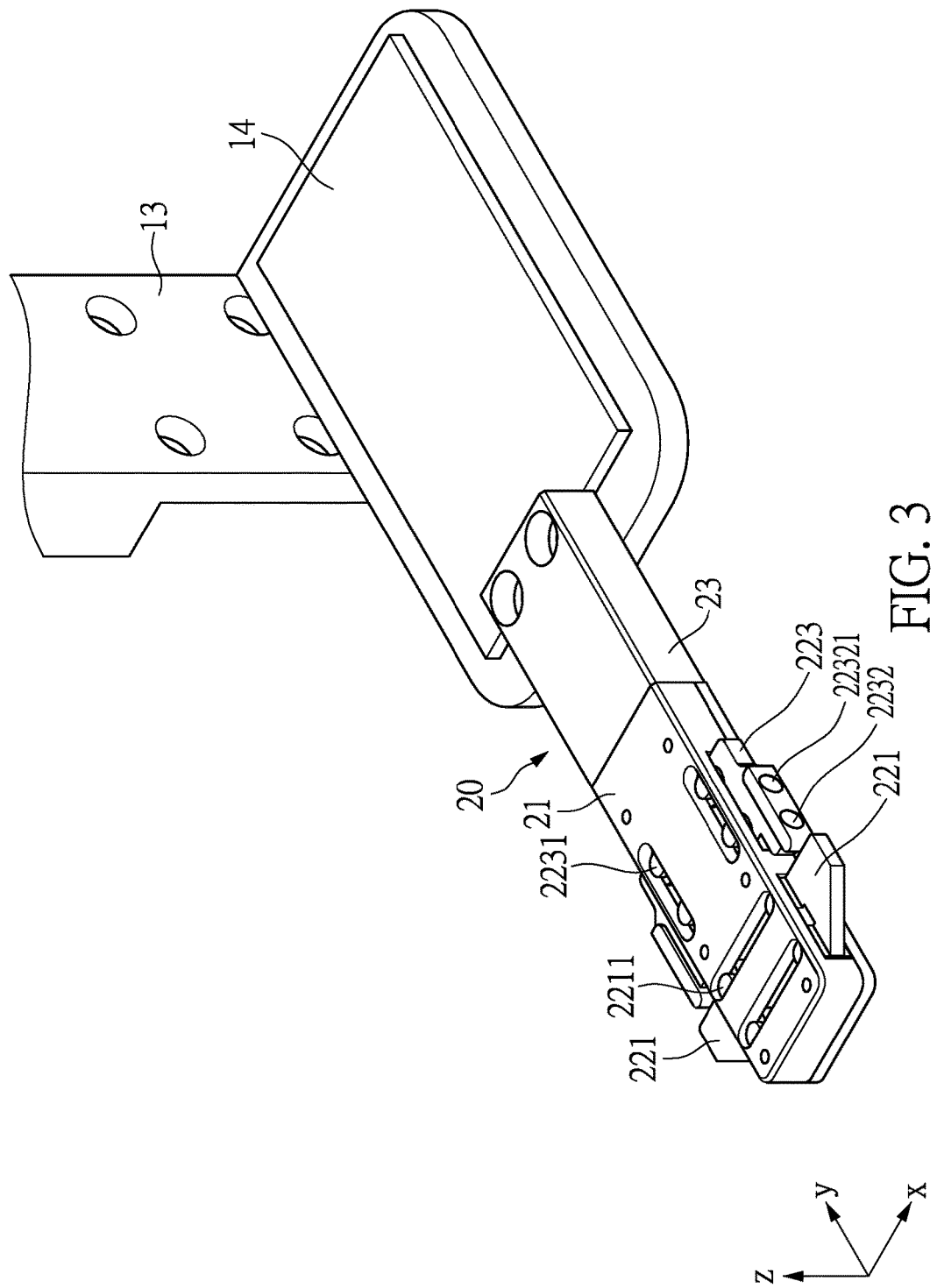
FIG. 3 is a schematic diagram of a connecting unit and a placing unit of the transportation system for paraffin embedded tissues of the instant disclosure.
Figure 4:
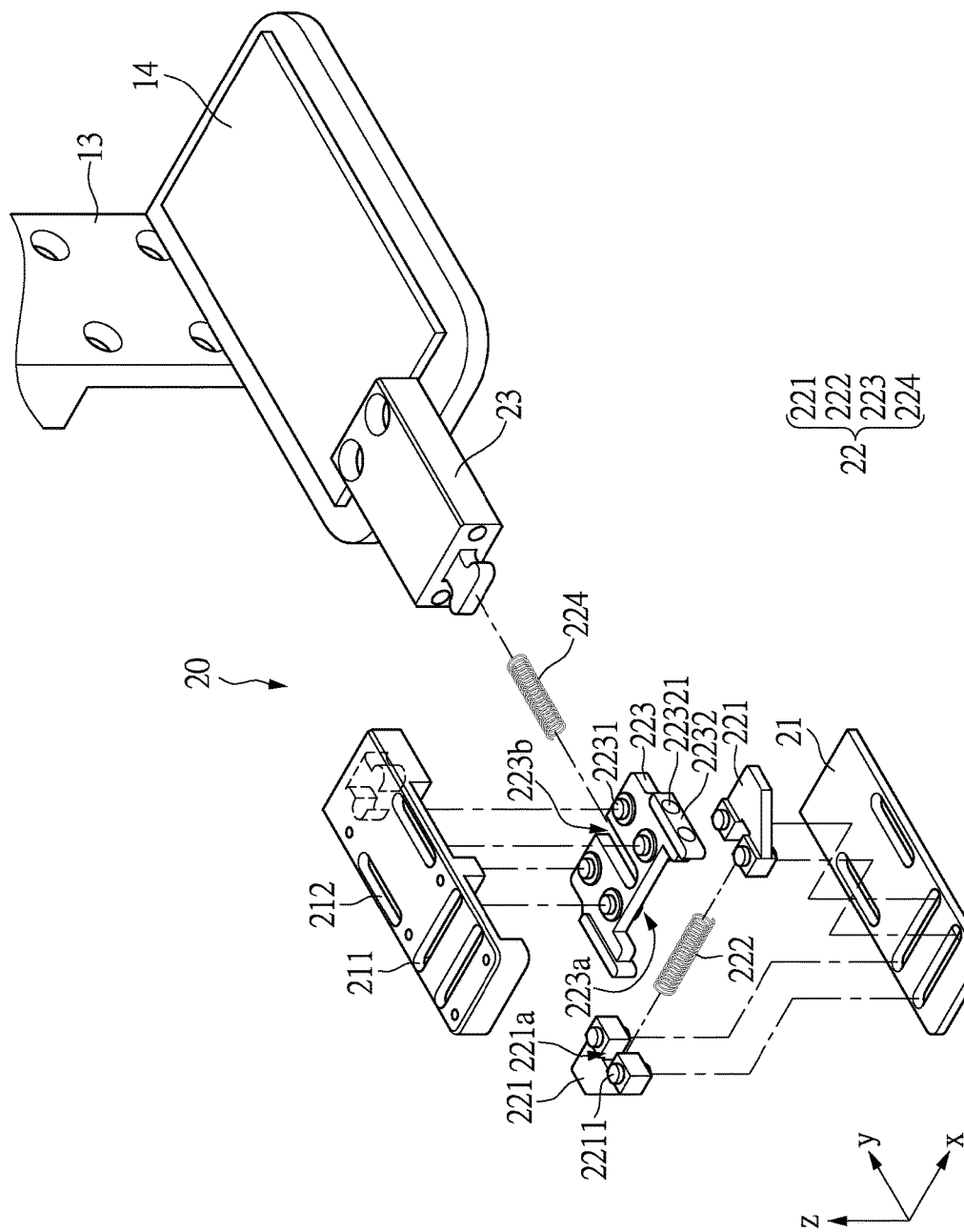
FIG. 4 is an exploded schematic view of the placing unit of the transportation system for paraffin embedded tissues of the instant disclosure.

FIG. 3 and FIG. 4 are an exploded view and an assembled view of the placing unit 20, respectively. The placing unit 20 comprises a body 21, a positioning component 22 and a buffering unit 23. The positioning component 22 is disposed on the body 21, and the positioning component 22 can optionally engage with or separate from the limiting slot 41b of the bearing unit 40.

The body 21 comprises a plurality of first limiting slots 211 and a plurality of second limiting slots 212. The first limiting slots 211 can be disposed substantially parallel to each other, and the second limiting slots 212 can be disposed substantially parallel to each other. The long axis of the first limiting slots 211 and the long axis of the second limiting slots 212 are not parallel to each other. For example, the first limiting slots 211 are disposed along the X axis, and the second limiting slots 212 are disposed along the Y axis. Each of the first limiting slots 211 and each of the second limiting slots 212 can be disposed separately and not be communicated with each other, and the direction of the long axis of each of the first limiting slots 211 can be substantially parallel to the inserting direction of the placing unit 20 into the inserting slot PS (i.e., the Y axis direction). The details of the placing unit 20 and the inserting slot PS will be described later.

The positioning component 22 can comprise two first positioning members 221, a first elastic member 222, a second positioning member 223 and a second elastic member 224. The two first positioning members 221 are disposed in the body 21 and spaced apart from each other, and a portion of each of the two first positioning members 221 are exposed from two opposite sidewalls of the body 21. Each of the first positioning members 221 has four first convex portions 2211, and two of the first convex portions 2211 disposed on the same side are spaced apart from each other. The two first convex portions 2211 disposed on the same side are correspondingly pivoted to the two first limiting slots 211. Therefore, each first positioning member 221 can move relative to the body 21 along the X axis by the coordination between the first convex portions 2211 and the first limiting slots 211. The two first positioning members 221 can move toward each other or away from each other.

The first elastic member 222 is disposed between the two first positioning members 221, and the two ends of the first elastic member 222 abut the two first positioning members 221. Each of the first positioning members 221 has a limiting groove 221a, and a portion of each end of the first elastic member 222 can be correspondingly located in the two limiting grooves 221a of the first positioning member 221, thereby maintaining the movement of the first elastic member 222 along a same axis during the processes of compressing and recovering. When the two first positioning members 221 are subjected to an external force and move toward each other, the first elastic member 222 is compressed and provides an elastic recovering force to the two first positioning members 221. The two first positioning members 221 can return to the original locations by the elastic recovering force when the external force is no longer provided.

The second positioning member 223 is disposed in the body 21 and has four second convex portions 2231, with two of the second convex portions 2231 being disposed on the same side and being spaced apart from each other. The two second convex portions 2231 disposed on the same side are correspondingly pivoted to the two second limiting slots 212. Therefore, each of the second positioning members 223 can move relative to the body 21 along the Y axis by the coordination between the second convex portions 2231 and the second limiting slots 212. The second positioning member 223 can move toward the two first positioning members 221 or away from the two first positioning members 221.

Figure 5:
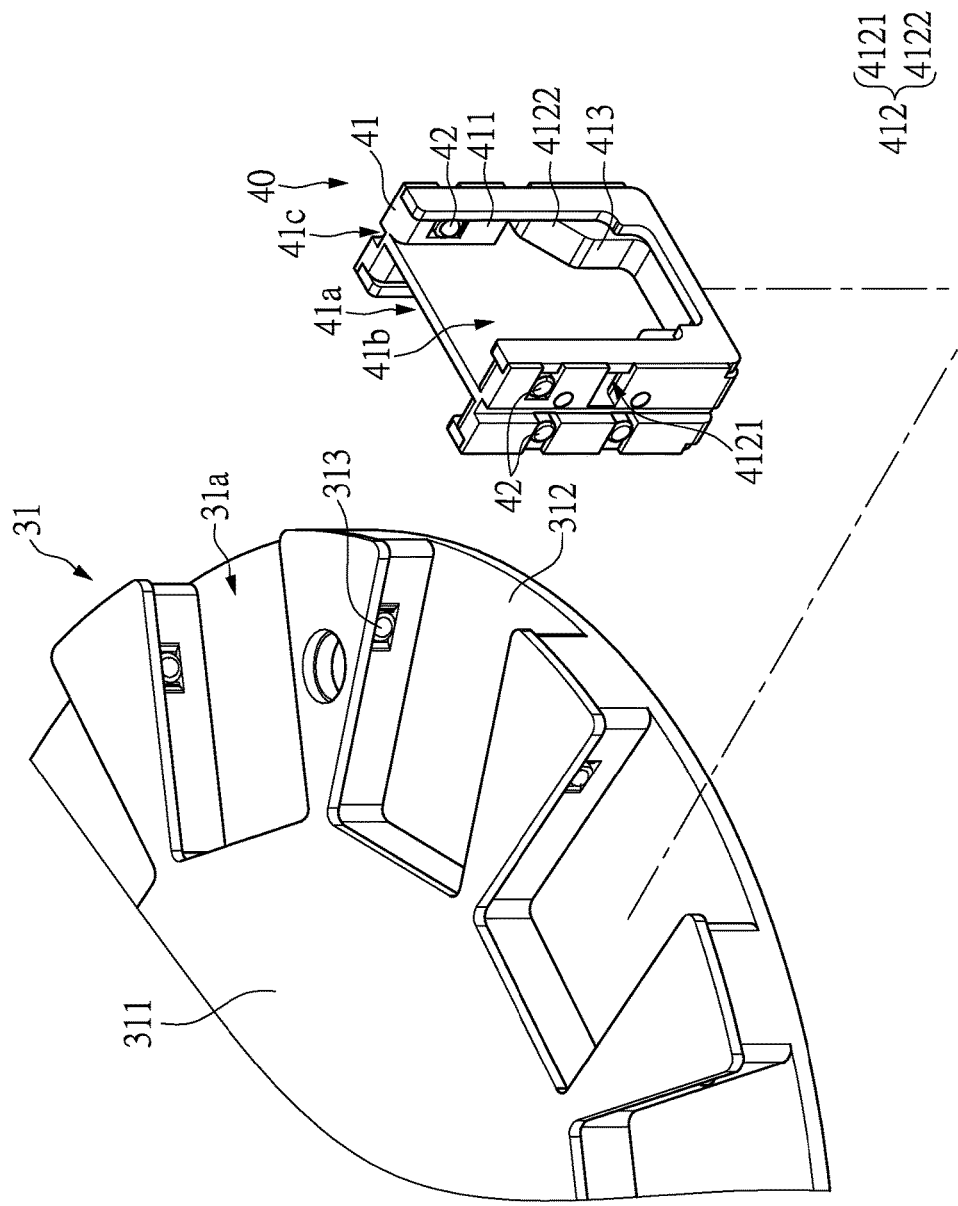
FIG. 5 is a schematic view of a rotation plate and a bearing unit of the transportation system for paraffin embedded tissues of the instant disclosure.

The second positioning member 223 further has two engaging portions 2232 correspondingly exposed from two opposite sidewalls of the body 21, and the two engaging portions 2232 are adjacent to the two first positioning members 221 exposed from the body 21. The two engaging portions 2232 exposed from the body 21 can optionally abut the two first positioning members 221 exposed from the body 21. Each of the engaging portions 2232 has two engaging slots 22321, and the location of the two engaging slots 22321 of the two engaging portions 2232 substantially corresponds to each other. The engaging portions 2232 can engage with the positioning unit 42 of the bearing unit 40 (as shown in FIG. 5) through the engaging portions 2232 and the engaging slots 22321, thereby limiting the movement of the second positioning member 223 relative to the bearing unit 40.

The end of the second positioning member 223 adjacent to the two first positioning members 221 has an engaging slot 223a. The other end of the second positioning member 223 can have a limiting groove 223b. The engaging slot 223a can receive the two first positioning members 221 moving toward each other, and the engaging slot 223a can limit the two received first positioning members 221 from moving away from the body 21. In other words, the two received first positioning members 221 are unable to move along the X axis. When the two first positioning members 221 are received in the engaging slot 223a, the first elastic member 222 is compressed and provides the two first positioning members 221 with an elastic recovering force. The two first positioning members 221 abut the sidewalls of the engaging slot 223a, and hence, the two first positioning members 221 are securely engaged in the engaging slot 223a. In other words, the second positioning member 223 can optionally limit the two first positioning members 221 from moving away from the body 21 when the first elastic member 222 is compressed.

The second elastic member 224 is disposed on the body 21. An end of the first positioning member 221 abuts the second positioning member 223, and a portion of the second elastic member 224 can be disposed in the limiting groove 223b for maintaining the second elastic member 224 to move along a same axis during the processes of compressing and recovering. The other end of the second elastic member 224 is fixed on the body 21, for example, the other end of the second elastic member 224 and the buffering unit 23 are fixed reciprocally. When the two first positioning members 221 are received in the engaging slot 223a, the second elastic member 224 can be compressed for providing a recovering force to the second positioning member 223 by the coordination of the two second limiting slots 212. Therefore, the sidewalls of the engaging slot 223a abut the two first positioning members, thereby allowing the second positioning member 223 to steadily engage with the two first positioning members 221.

An end of the buffering unit 23 is fixed on the connecting unit 14 for being connected to the horizontal moving assembly 131. The other end of the buffering unit 23 is connected to the body 21. The body 21 can move forward (along the Y axis direction in FIG. 4) and insert into a inserting slot PS, and the body 21 can swing upwardly or downwardly relative to the buffering unit 23 within a predetermined range. In other words, based on the buffering unit 23, the placing unit 20 can move freely in the un-inserted direction. Therefore, the placing unit 20 can be guided to steadily insert into the inserting slot PS from the predetermined range.

Figure 6:
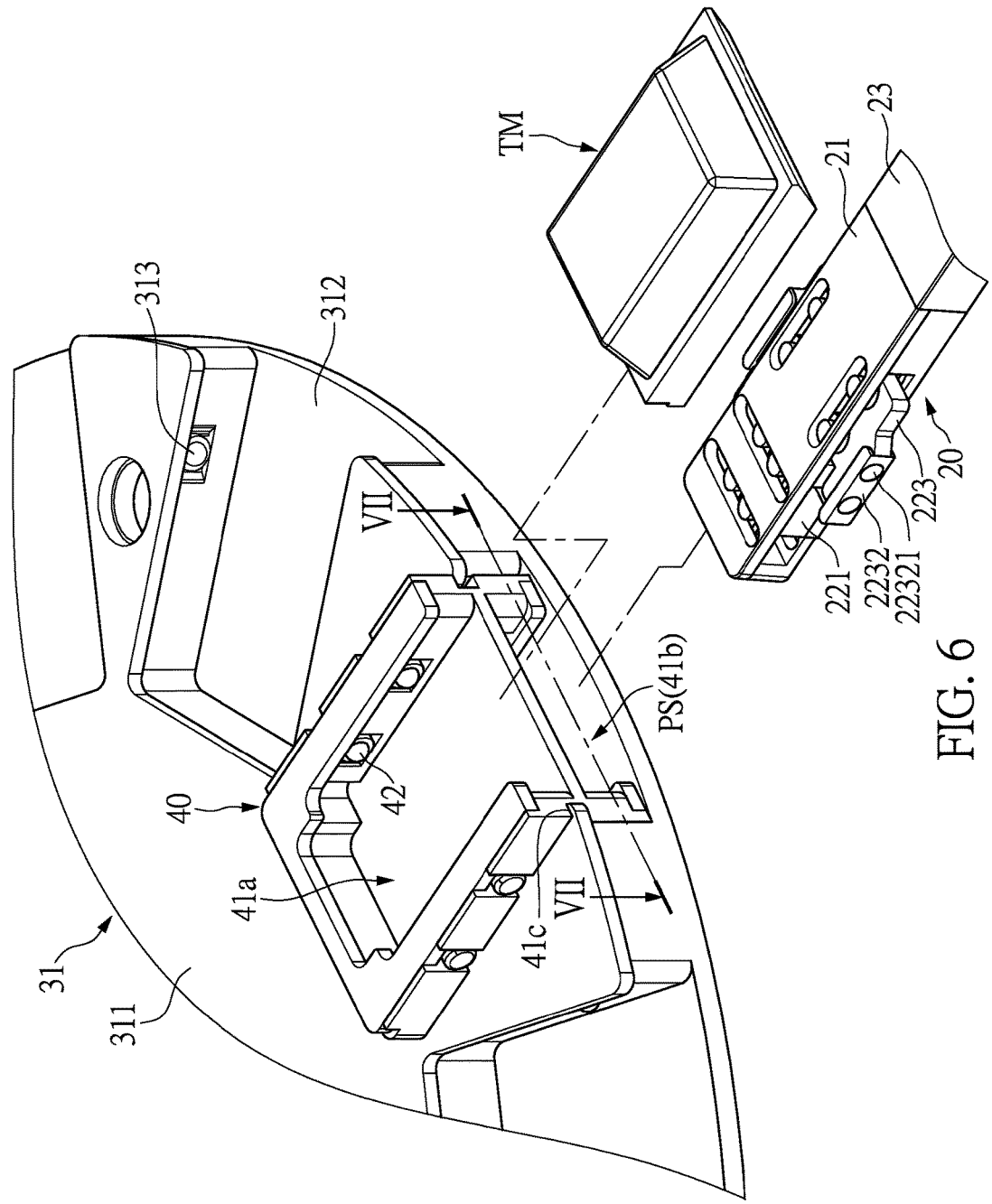
FIG. 6 is an exploded schematic view of the rotation plate, the placing unit, the bearing unit and the paraffin embedded tissues of the transportation system for paraffin embedded tissues of the instant disclosure.

Referring to FIG. 5 and FIG. 6. The rotation plate 31 of the storage device 30 can comprise a top cover 311 and a base 312. The top cover 311 and the base 312 together form a plurality of receiving slots 31a, and a portion of the top cover 311 exposes the receiving slot 31a. Two engaging units 313 (such as ball springs) opposite to each other are disposed in each receiving slot 31a.

The bearing unit 40 has a bearing body 41. Two opposite sides of the bearing body 41 have a bearing slot 41a and a limiting slot 41b respectively formed inwardly, and another two opposite sides of the bearing body 41 each has a guiding slot 41c. The guiding slots 41c can engage with the portion of the top cover 311 exposed from the receiving slot 31a. The bearing unit 40 can properly enter and be fixed in the receiving slot 31a by the guidance of the two guiding slots 41c and the portion of the top cover 311 exposed from the receiving slot 31a. When the bearing unit 40 is fixed in the receiving slot 31a, the limiting slot 41b of the bearing unit 40 and the base 312 of the rotation plate 31 together form an inserting slot PS for the placing unit 20 to insert in. The bearing slot 41a is used for receiving the paraffin embedded tissues TM, and the sidewalls of the bearing slot 41a has a plurality of positioning units 42 (such as ball springs), thereby assisting the paraffin embedded tissues TM to be fixed in the bearing slot 41a. The paraffin embedded tissues TM can have correspondingly engaging structures. It is worth mentioning that although the placing unit 20 is inserted into the inserting slot PS in the present embodiment, in other embodiments, the limiting slot 41b may not form the inserting slot PS with the base 312 so that the placing unit 20 can be directly inserted into the limiting slot 41b.

Figure 7:
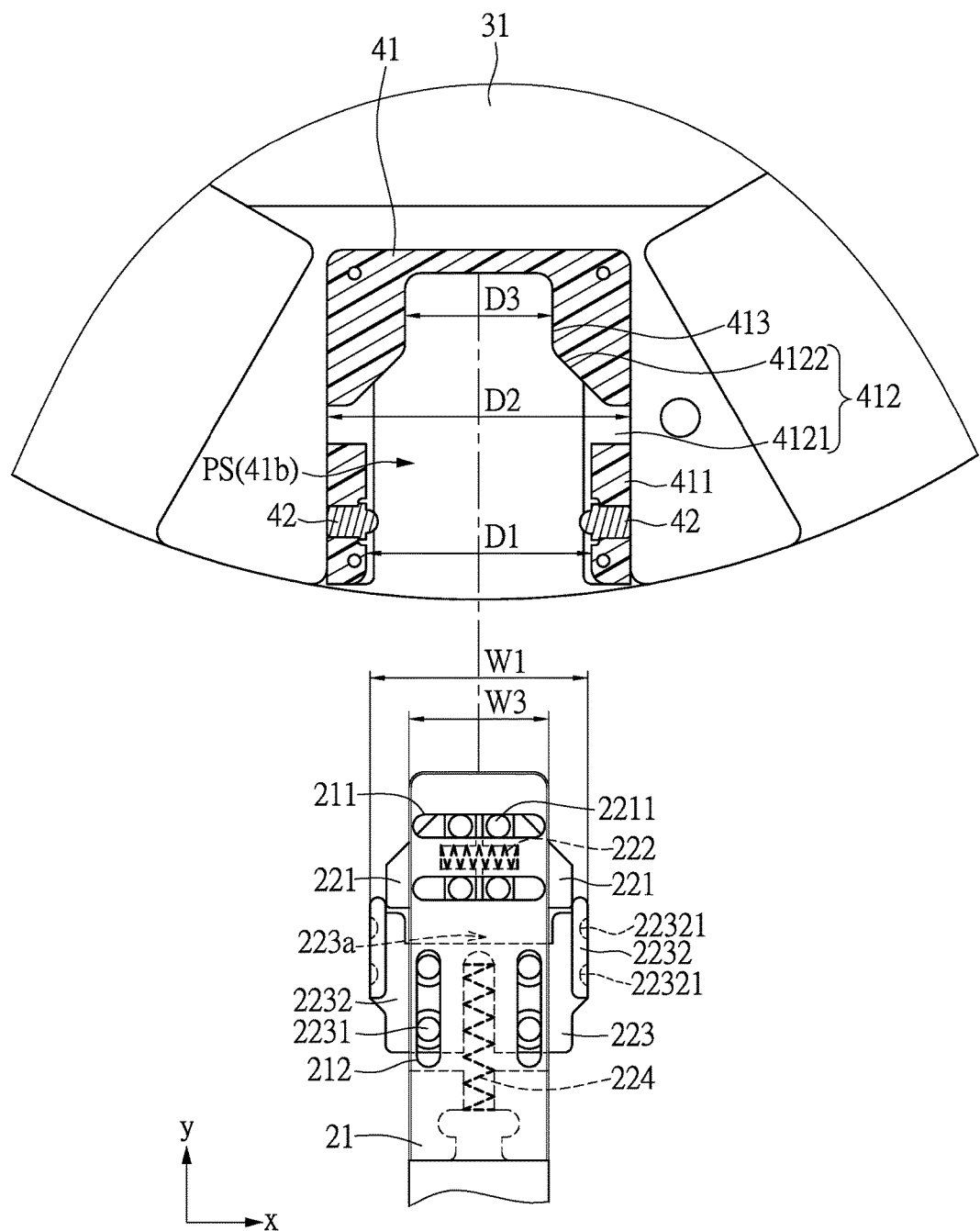
FIGS. 7 to 11 are operation schematic views of the separation of the bearing unit and the rotation plate controlled by the placing unit in the transportation system for paraffin embedded tissues of the instant disclosure.

FIG. 7 shows the sectional view of the bearing unit 40 taken from VII-VII sectional line of FIG. 6. The bearing body 41 has two first guiding sidewalls 411 opposite to each other, two limiting structures 412 opposite to each other and two second guiding sidewalls 413 opposite to each other. The first guiding sidewalls 411, the limiting structures 412 and the second guiding sidewalls 413 together form the limiting slot 41b, and the two first guiding sidewalls 411 are adjacent to the opening of the limiting slot 41b (the opening of the limiting slot 41b communicated with the external space when the limiting slot 41b is fixed on the rotation plate 31). The limiting structures 412 are located between the two first guiding sidewalls 411 and the two second guiding sidewalls 413. The two first guiding sidewalls 411 can each have a positioning unit 42 (such as a ball spring). Each of the limiting structures 412 includes a limiting receiving slot 4121 and a guiding structure 4122. The limiting receiving slot 4121 is disposed adjacent to the first guiding sidewalls 411, and the guiding structure 4122 is disposed adjacent to the second guiding sidewalls 413. In other words, when the placing unit 20 is controlled and inserted into the inserting slot PS, the placing unit 20 passes through the first guiding sidewalls 411, the limiting receiving slot 4121, the guiding structure 4122 and the second guiding sidewalls 413 in sequence.

The distance between the two first guiding sidewalls is defined as a first distance D1, the distance between the two limiting receiving slots 4121 is defined as a second distance D2, and the distance between the two second guiding sidewalls 413 is defined as a third distance D3. The first distance D1 can be substantially equal to the third distance D3, and the second distance D2 is larger than the first distance D1 and the third distance D3.

Figure 13:
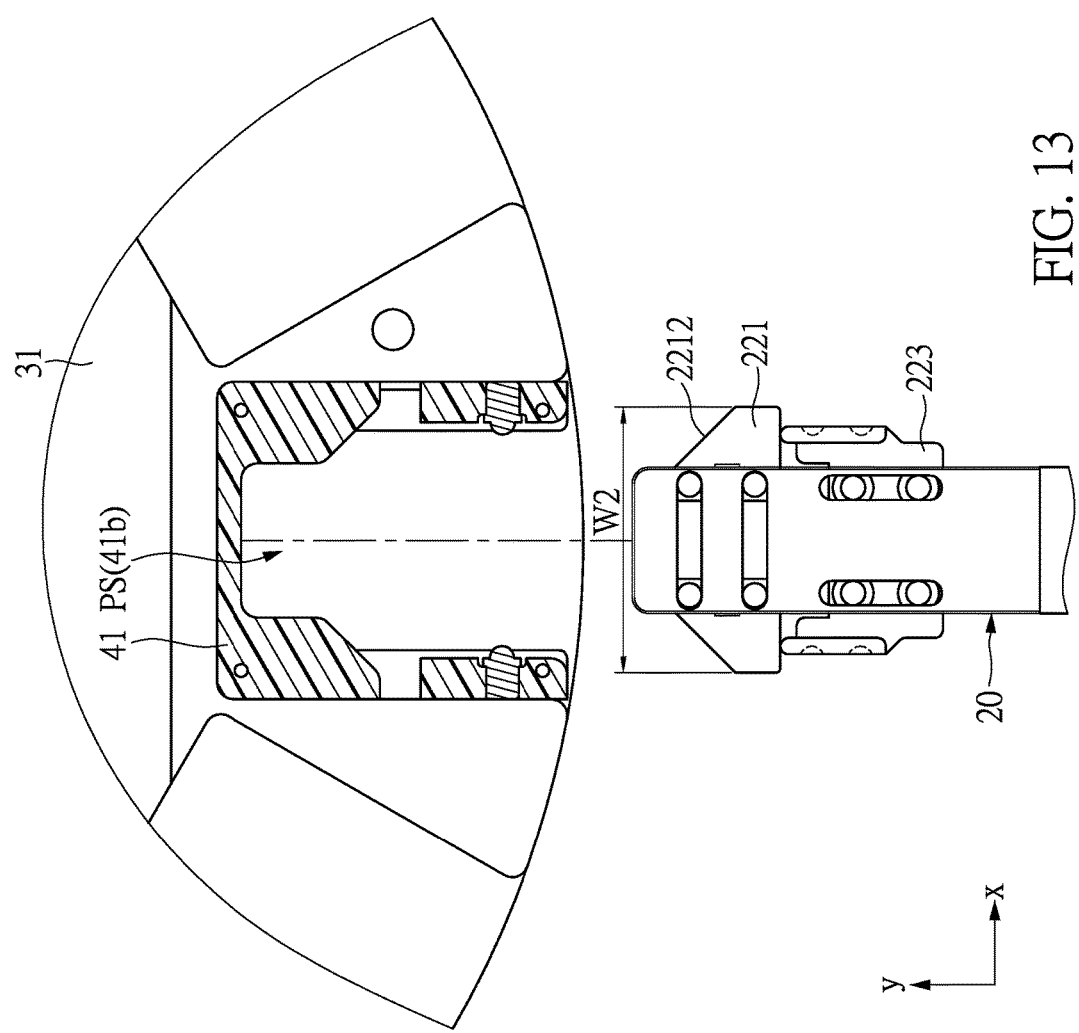
FIG. 13 and FIG. 14 are schematic views in a state that the placing unit and the rotation plate are inserted and connected to each other in the transportation system for paraffin embedded tissues of the instant disclosure.

When the two first positioning members 221 are received in the engaging slot 223a, the surfaces having the engaging slots 22321 of the two engaging portions 2232 of the placing unit 20 has a first width W1. As shown in FIG. 13, when the first elastic member 222 is not compressed, the two first positioning members 221 outside of the engaging slot 223a each have a surface separated from one another, and the distance between the surfaces is defined as a second width W2. The end of the body 21 that enters the inserting slot PS first has a width defined as a third width W3. The first width W1 is not larger than the first distance D1, the second distance D2 or the third distance D3, and the second width W2 is larger than the first distance D1 and the third distance D3. The second width W2 is not larger than the second distance D2.

FIG. 7 to FIG. 11 show the procedure in which the placing unit 20 is inserted in the inserting slot PS and engaged with the bearing unit 40, and the placing unit 20 separates the bearing unit 40 from the receiving slot 31a. First, as shown in FIG. 7, the two first positioning members 221 are received in the engaging slot 223a of the second positioning member 223. The two first positioning members 221 are exposed from the body 21 but do not protrude from the two engaging portions 2232. In this state, the maximum width of the placing unit 20 is the first width W1, and since the first width W1 is not larger than the first distance D1, the placing unit 20 can be driven by the body 21 and the moving assembly 13 to insert into the inserting slot PS. In this state, the first elastic member 222 is compressed, the two first positioning members 221 abut the sidewalls of the engaging slot 223a, and the second elastic member 224 can also be compressed. Therefore, the second elastic member 224 can allow the second positioning member 223 to abut the two first positioning members 221, thereby firmly receiving the two first positioning members 221 in the engaging slot 223a.

Figure 8:
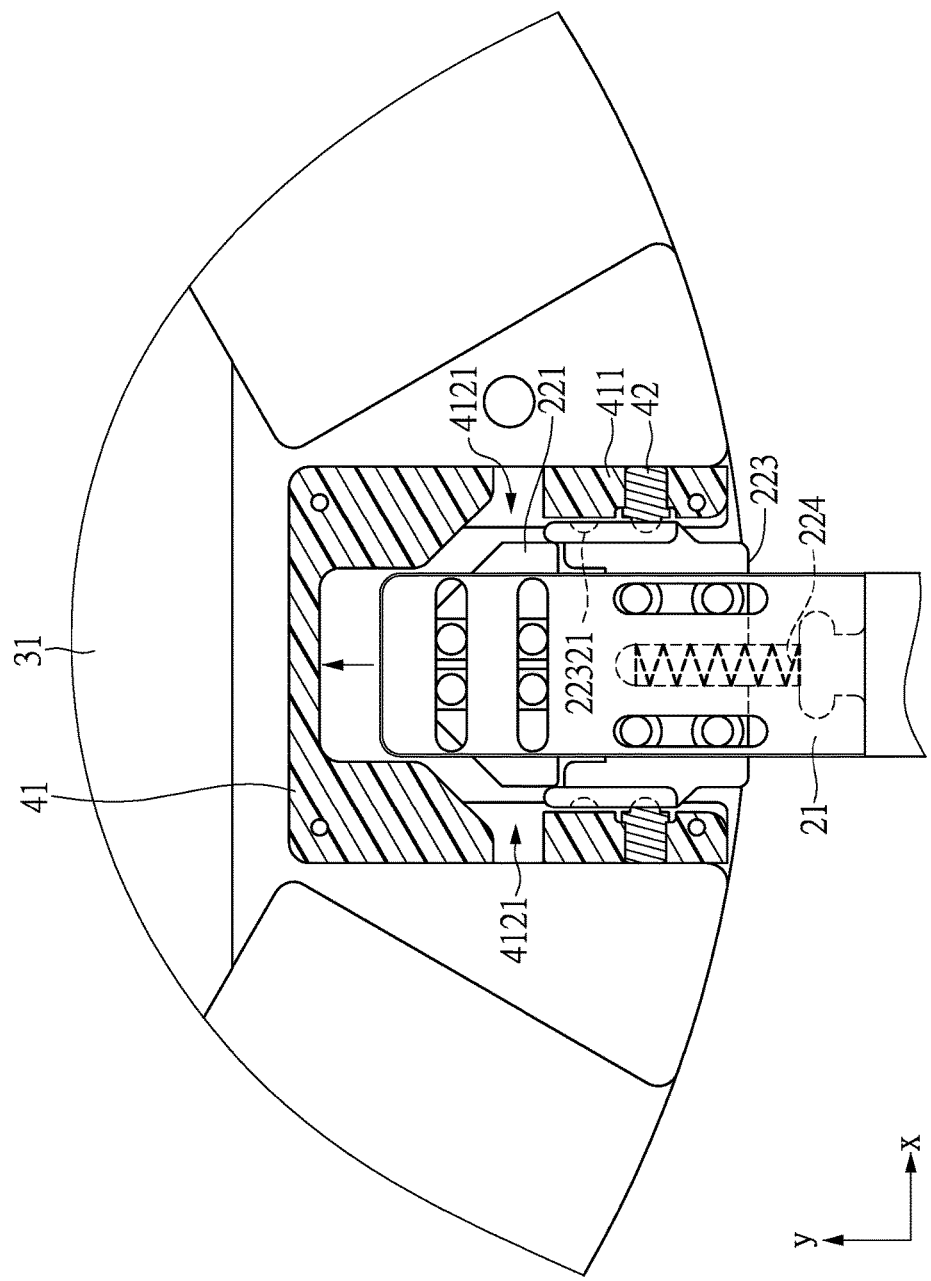

As shown in FIG. 7 and FIG. 8, during the procedure in which the placing unit 20 (controlled by the horizontal moving assembly 131) enters the inserting slot PS, until the engaging slots 22321 of each of the engaging portions 2232 engages with the engaging units 313 in the limiting slot 41b, the two first positioning members 221 are limited by the engaging slot 223a and do not protrude from the two engaging portions 2232. In the state shown in FIG. 8, the two first positioning members 221 are limited by the engaging slot 223a and the first elastic member 222 is compressed. When the engaging groove 22321 of the second positioning member 223 engages with the engaging unit 313, the second elastic member 224 can also be compressed.

Figure 9:
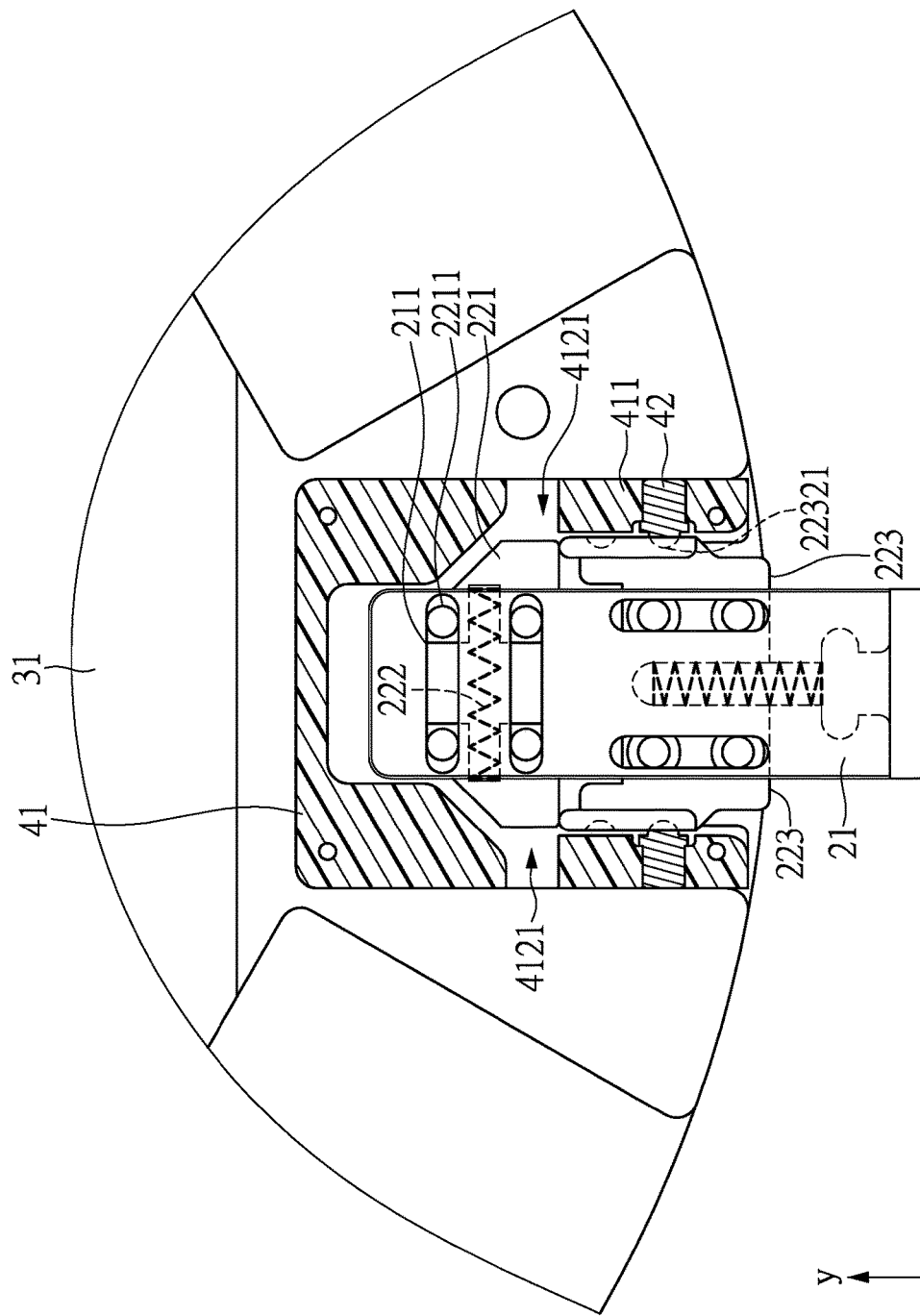

As shown in FIG. 8 and FIG. 9, when the engaging slots 22321 and the engaging units 313 engage with each other, and the placing unit 20 continues to move into the inserting slot PS by the horizontal moving assembly 131 of the placing assembly 10, the two first positioning members 221 are limited by the first convex portions 2211 and the two first limiting slots 211 and move toward the inserting slot PS along with the body 21. The second positioning member 223 does not move with the body 21 since the second positioning member 223 is limited by the pivotal relationship between the second convex portions 2231 and the second limiting slots 212 and the engagement relationship between the engaging slots 22321 and the engaging units 313. In other words, when the engaging slots 22321 of the second positioning member 223 are engaged with the engaging units 313 and the placing unit 20 is controlled for moving forwardly (along the Y axis direction shown in the figures), the two first positioning members 221 and the body 21 will move forwardly relative to the second positioning member 223.

Figure 10:
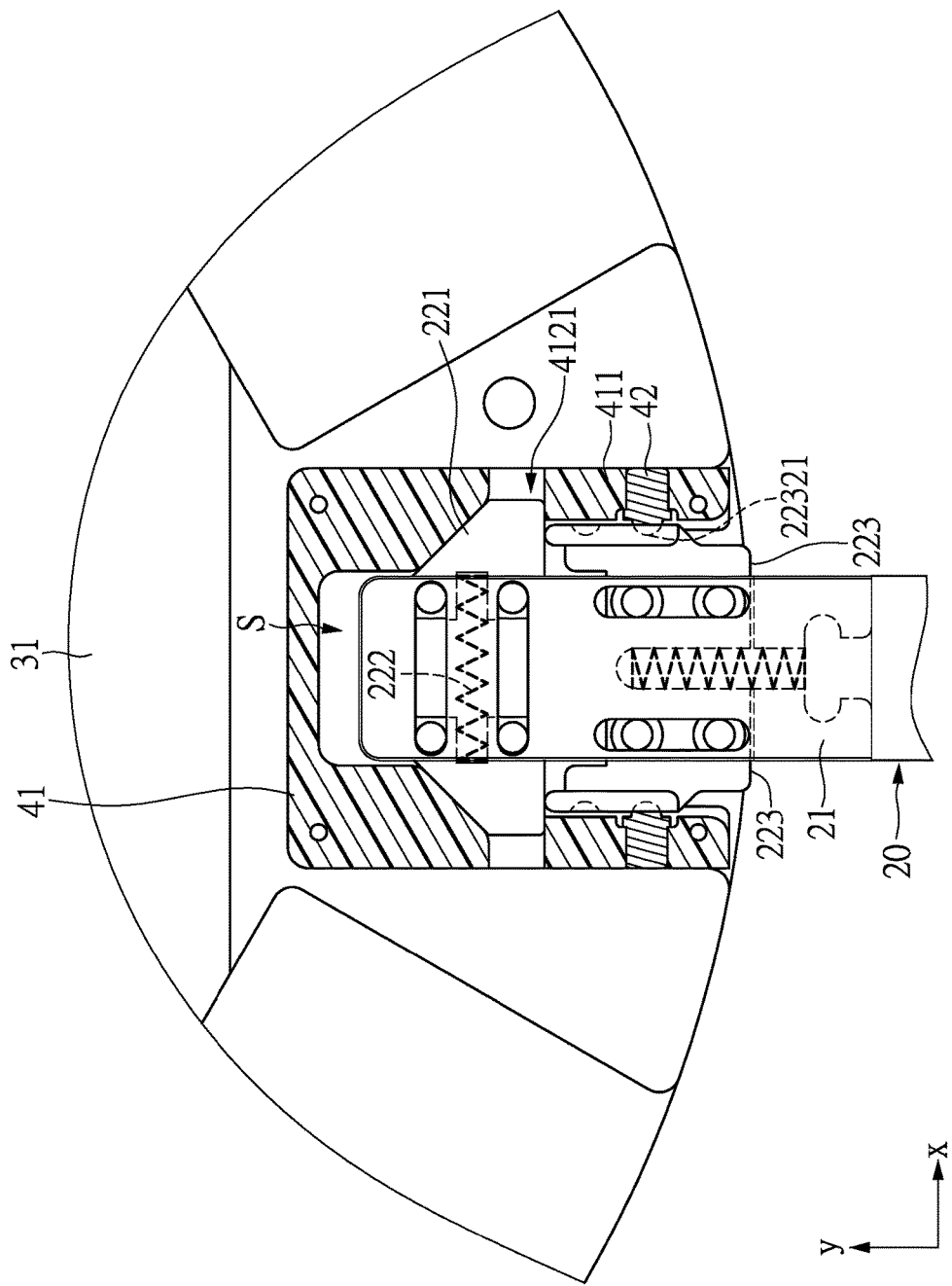

As shown in FIG. 9 and FIG. 10, after the body 21 and the two first positioning members 221 move forward relative to the second positioning member 223, the two first positioning members 221 are separated from the engaging slot 223a. Therefore, the two first positioning members 221 are no longer limited by the engaging slot 223a. The two first positioning members 221 are subject to the elastic recovering force of the first elastic member 222 and move away from the body 21, thereby allowing a portion of each of the first positioning member 221 to engage with the limiting structure 412. In other words, the portion of each of the first positioning member 221 can engage with the corresponding limiting receiving slot 4121, and the portion of each of the first positioning member 221 abuts the corresponding guiding structure 4122. The compression amount of the first elastic member 222 when the positioning component 22 and the limiting structure 412 are engaged with each other is smaller than the compression amount of the first elastic member 222 when the positioning component 22 and the limiting structure 412 are separated from each other.

As shown in FIG. 10, when the first elastic member 222 is not compressed, the two first positioning members 221 are spaced apart from each other for a longest distance (i.e., the second width W2). Since the second width W2 is larger than the distance between the two first guiding sidewalls 411 (the first distance D1), under this condition, the two first positioning members 221 and the two first guiding sidewalls 411 abut each other to limit the placing unit 20 from moving away from the bearing unit 40. In other words, in the state shown in FIG. 10, the placing unit 20 and the bearing unit 40 engage with each other.

Figure 11:
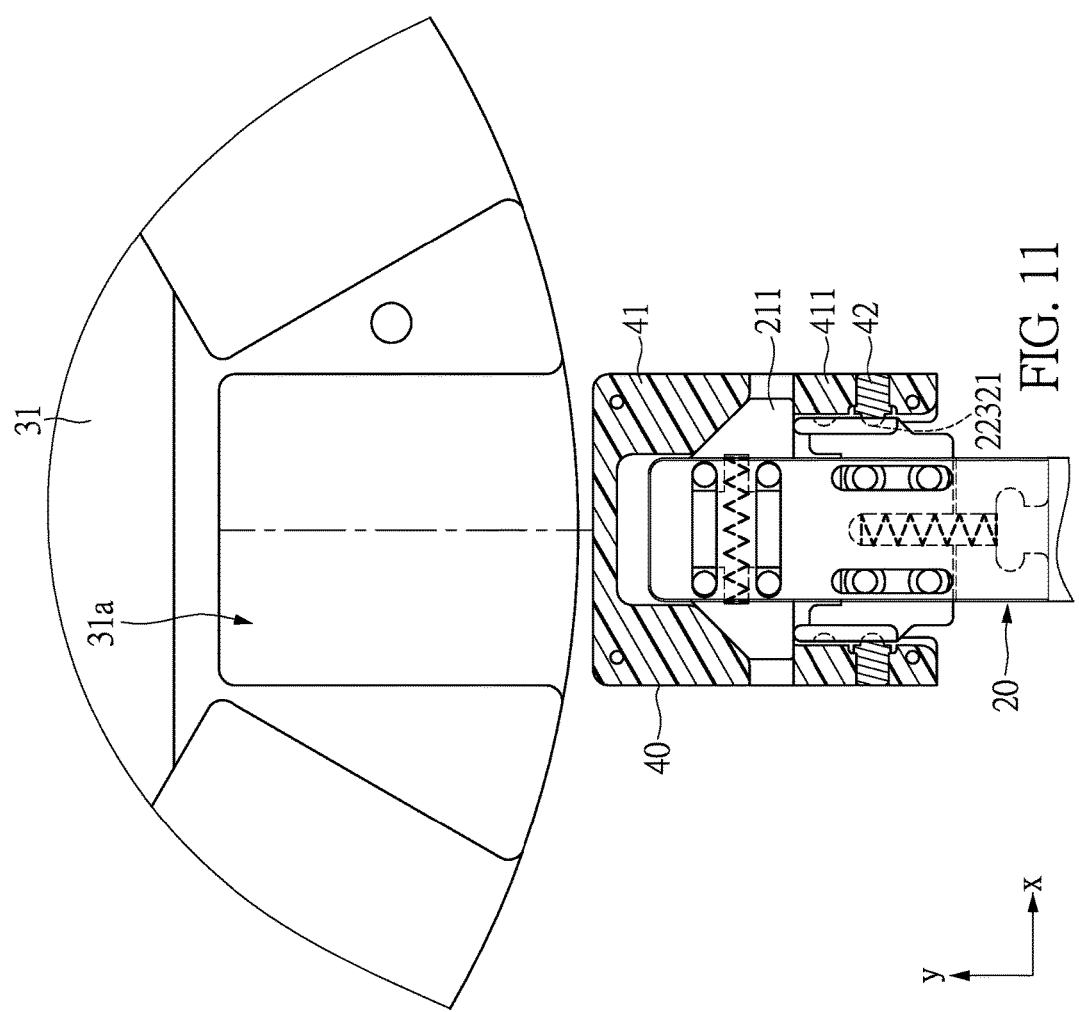

As shown in FIG. 10 and FIG. 11, when the placing unit 20 and the bearing unit 40 engage with each other, the horizontal moving assembly 131 can move the placing unit 20 toward the direction away from the rotation plate 31, thereby separating the placing unit 20 and the bearing unit 40 engaged with the placing unit 20 from the receiving slot 31a. The rotation assembly 12 and the moving assembly 13 can transport the placing unit 20 and the bearing unit 40 to specific locations.

Referring to FIG. 1, by the coordination of the placing unit 20, the receiving slot 31a and the bearing unit 40, when the processing apparatus T has a receiving slot same as the receiving slot 31a, the placing assembly 10 can transport the bearing unit (not shown) of the receiving slot (not shown) of the processing apparatus T and the paraffin embedded tissues thereon to one of the receiving slots 31a of the rotation plate 31. The placing assembly 10 may also transport the bearing unit 40 in one of the receiving slots 31a of the rotation plate 31 and the paraffin embedded tissues TM thereon to the processing apparatus T. Therefore, the overall detecting speed and performance can be enhanced.

When the rotation assembly 12 and the moving assembly 13 move the placing unit 20 to transport a bearing unit 40 (as shown in FIG. 11) and correspondingly insert the bearing unit 40 within a predetermined receiving slot 31a of the rotation plate 31 (as shown in FIG. 10), the horizontal moving assembly 131 of the placing assembly 10 can move the placing unit 20 relative to the bearing unit 40 to separate the placing unit 20 from the bearing unit 40. Specifically, as shown in FIG. 10, when the placing unit 20 and the bearing unit 40 engage with each other, a space between an end of the placing unit 20 opposite to the end connected to the connecting unit 14 and the deepest location of the limiting slot 41b (the inserting slot PS) form a moving gap S. When the placing unit 20 and the bearing unit 40 engage with each other, the horizontal moving assembly 131 of the placing assembly 10 can still move the placing unit 20 towards the limiting slot 41b As shown in FIG. 11, when the placing unit 20 and the bearing unit 40 engage with each other, the horizontal moving assembly 131 of the placing assembly 10 can control the placing unit 20 to move toward the moving gap S, and the body 21 and each of the first positioning members 221 are driven to move toward the moving gap S. Meanwhile, each of the first positioning members 221 is abutted by the corresponding guiding structure 4122 so that the two first positioning members 221 move toward each other, thereby compressing the first elastic member 222. When the two positioning members 221 continue to be abutted by the guiding structure 4122 and move towards to each other, the distance between the surfaces of two positioning members 221 having the engaging slots 22321 located thereon decreases from the second width W2 shown in FIG. 13 to the first width W1 shown in FIG. 7. Meanwhile, the second positioning member 223 is driven by the body 21 and the second elastic member 224 for abutting the two first positioning members 221.

Figure 12:
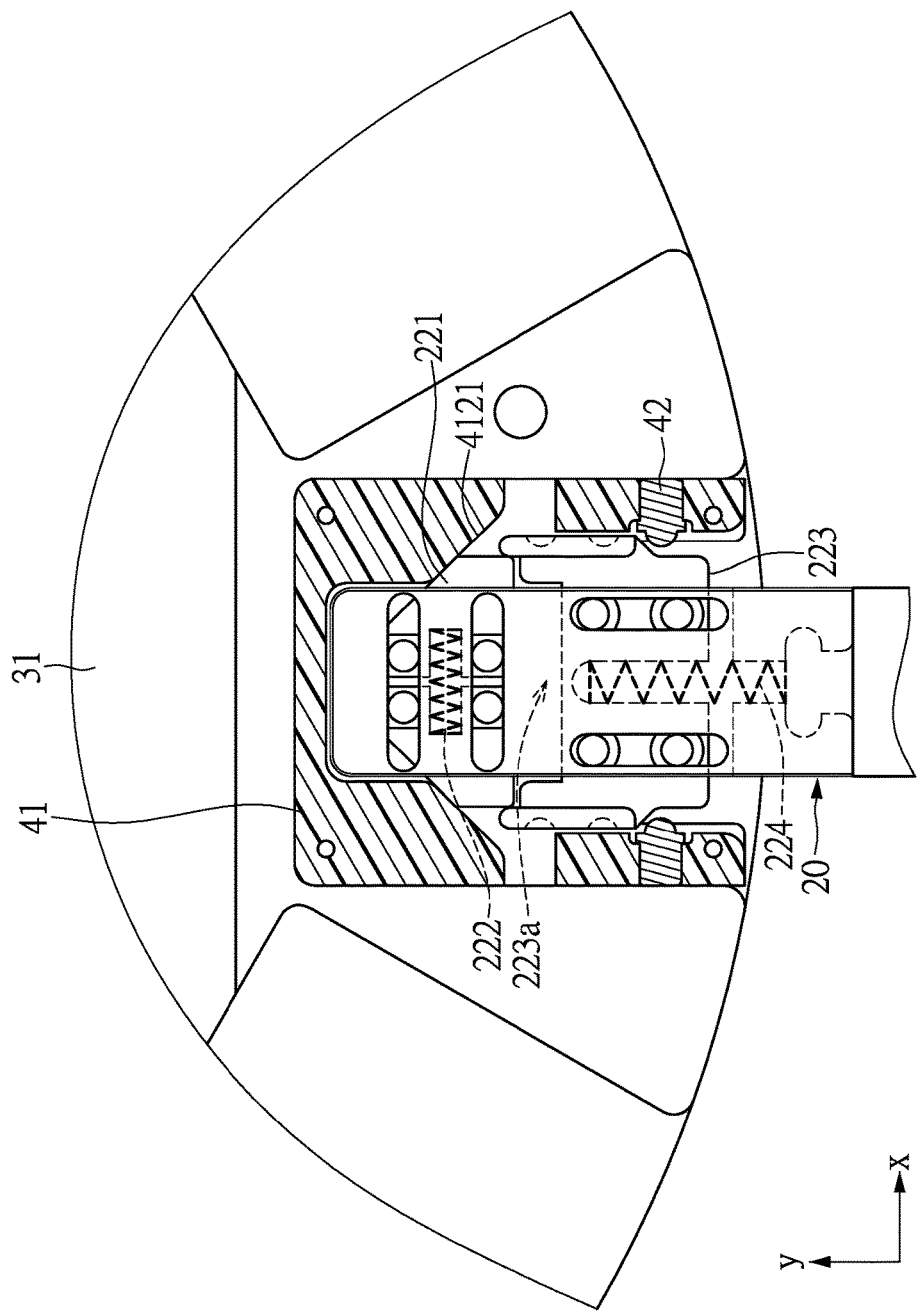
FIG. 12 is a schematic view in a state that the placing unit and the bearing unit are separated from each other in the transportation system of the paraffin embedded tissues for instant disclosure.

When the distance between the two positioning members 221 reduce from the first width W1 to the second width W2, the two positioning members 221 are received in the receiving slots 223a of the second positioning member 223, and the two first positioning members 221 are limited by the receiving slots 223a again. Therefore, the placing unit 20 can change from a state that is in engagement with the bearing unit 40 to a state that is separated from the bearing unit 40. The horizontal moving assembly 131 of the placing assembly 10 can move the placing unit 20 away from the bearing unit 40 for separating the placing unit 20 from the inserting slot PS. Referring to FIG. 10 and FIG. 12, when the placing unit 20 and the bearing unit 40 are engaged with each other, the horizontal moving assembly 131 of the placing assembly 10 can move the placing unit 20 forward to allow the two first positioning members 221 to be received in the receiving slots 223a, thereby removing the engagement between the placing unit 20 and the bearing unit 40 to separate the placing unit 20 from the inserting slot PS.

Figure 14:
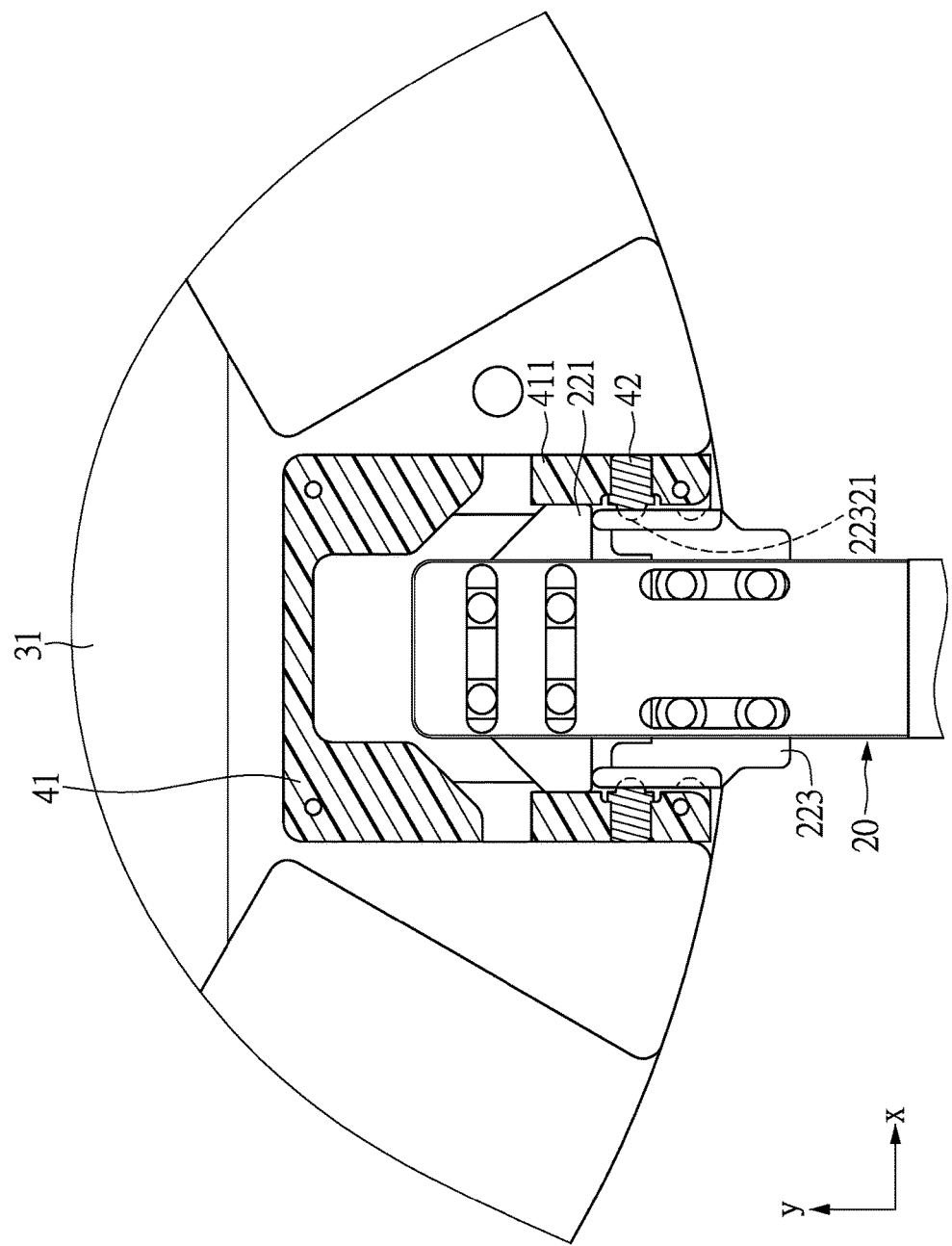

Referring to FIG. 13 and FIG. 14. In other embodiments, before the placing unit 20 enters the inserting slot PS, the two first positioning members 221 can be separated from the receiving slots and are exposed from the two opposite sides of the body 21. That is, before the placing unit 20 enters the inserting slot PS, the first elastic member 222 is not compressed. The two first positioning members 221 exposed from the body 21 without being limited by the receiving slots 223a can abut the two first guiding sidewalls 411 by two inclined structures 2212 of the two first positioning members 221. Therefore, before the two first positioning members 221 enter the two limiting slots 4121, the two first positioning members 221 are limited by the two first guiding sidewalls 411, and hence, the first elastic member 222 is compressed. Afterwards, when the placing unit 20 is controlled to continuously move toward and into the limiting slot 41b, the two first positioning members 221 pass the two first guiding sidewalls 411 and engage in the two limiting slots 4121. Therefore, the placing unit 20 and the bearing unit 40 engage with each other. The subsequent movement and coordination of the placing unit 20 and the bearing unit 40 are described above.

Figure 15:
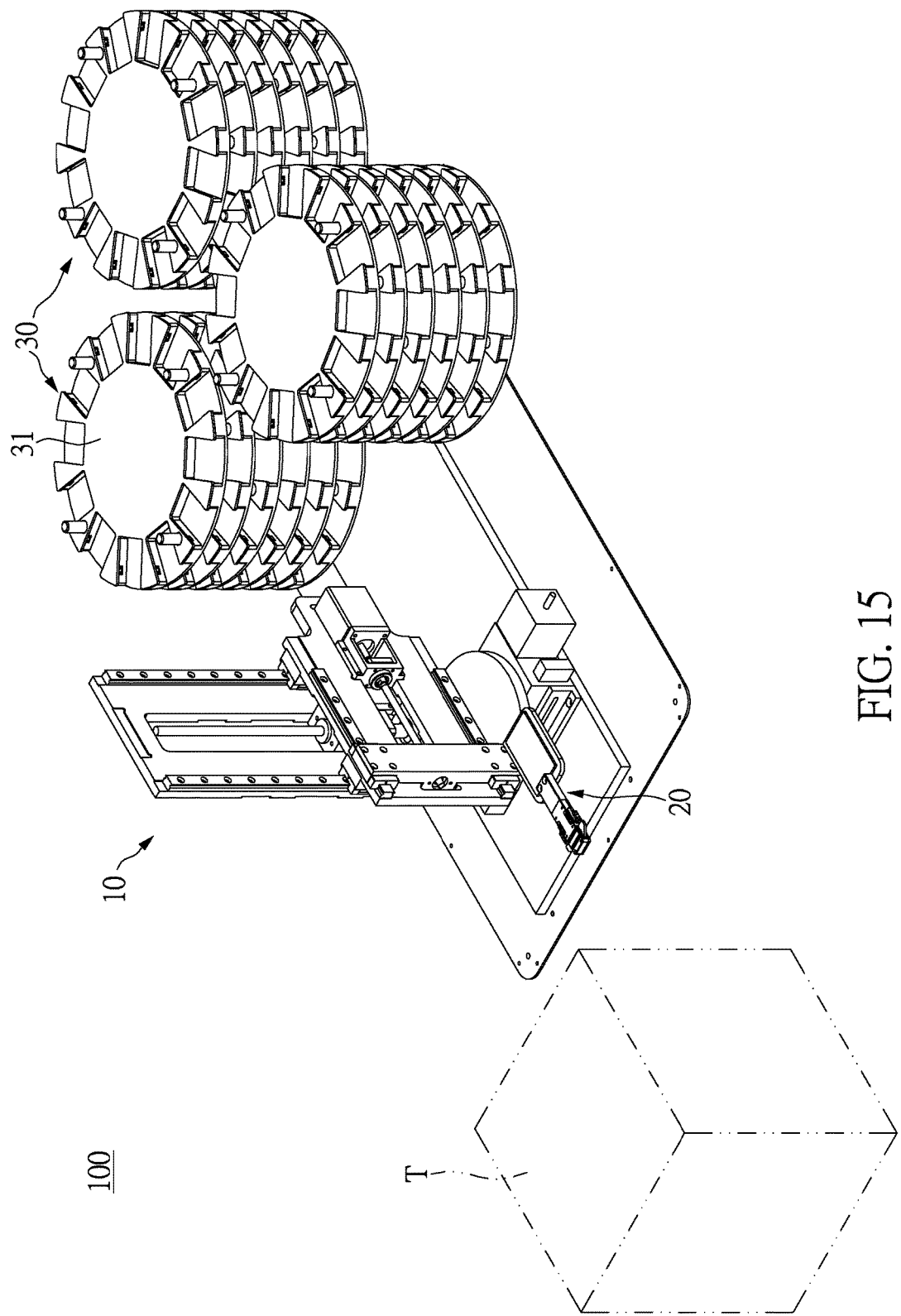
FIG. 15 is a schematic view of the transportation system for paraffin embedded tissues of another embodiment of the instant disclosure.

Referring to FIG. 15, in other applications, the transportation system for paraffin embedded tissues 100 can have a plurality of storage device 30 adjacent to each other, with the storage devices 30 being controlled to rotate and move correspondingly. For example, the storage devices 30 can rotate and move relative to each other. The structure and movements of each storage device 30 are described above.

In summary, the transportation system for paraffin embedded tissues of the instant disclosure can significantly increase the transportation speed of the paraffin embedded tissues.

The above-mentioned descriptions represent merely the exemplary embodiment of the present disclosure, without any intention to limit the scope of the instant disclosure thereto. Various equivalent changes, alterations or modifications based on the claims of the instant disclosure are all consequently viewed as being embraced by the scope of the instant disclosure.

What is claimed is:

1. A transporting system for paraffin embedded tissues, comprising:
    a placing assembly comprising:
        a horizontal moving assembly;
        a vertical moving assembly connected to the horizontal moving assembly;
        a rotation assembly connected to the horizontal moving assembly; and
        a placing unit, the placing unit being connected to the horizontal moving assembly and having a body and a positioning component including:
            two first positioning members disposed on the body, each exposed from the body and having a portion corresponding to two walls opposite to each other; and
            a first elastic member disposed on the body and between the two first positioning members, the first elastic member being configured to push the two first positioning members away from each other;
        wherein the horizontal moving assembly and the vertical assembly are configured to move the placing unit in horizontal and vertical directions, and the rotation assembly is configured to rotate the placing unit around a vertical axis;
    a bearing unit for receiving the paraffin embedded tissues, having a limiting slot, a limiting structure and a bearing slot configured to receive the paraffin embedded tissues, wherein the horizontal moving assembly is configured to place the placing unit into the limiting slot and remove the placing unit from the limiting slot for engaging the positioning component with the limiting structure and separating the positioning component from the limiting structure respectively; and
    a storage device disposed at a side of the placing assembly, the storage device having a rotation plate, the rotation plate having a plurality of receiving slots for storing the bearing unit;
    wherein the placing unit is configured to remove the bearing unit from the storage device and move the bearing unit to a processing apparatus located at another side of the placing assembly; the placing unit is configured to remove the bearing unit from the processing apparatus and transport the bearing unit to one of the receiving slots of the storage device;
    wherein when the positioning component and the limiting structure are engaged with each other, the horizontal moving assembly separates the placing unit and the bearing unit from the receiving slot.

2. The transporting system according to claim 1, wherein a compressed distance of the first elastic member when the positioning component and the limiting structure engage with each other is less than a compressed distance of the first elastic member when the positioning component and the limiting structure do not engage with each other.

3. The transporting system according to claim 2, wherein the positioning component further comprises a second positioning member disposed on the body, the second positioning member being configured to move the two first positioning members away from the body when the first elastic member is compressed, the placing unit being controlled by the horizontal moving assembly and separating from the limiting slot when the second positioning member limits the movement of the two first positioning members.

4. The transporting system according to claim 3, wherein the second positioning member has an engaging portion; the body and the two first positioning members is configured to move relative to the second positioning member; the limiting slot of each bearing unit has a positioning unit disposed therein, the engaging portion of the second positioning member being configured to engage with the positioning unit of each bearing unit; wherein when the placing unit is inserted in the limiting slot and the engaging portion of the second positioning member engages with the positioning unit, the body and the two first positioning members are controlled by the horizontal moving assembly and move relative to the second positioning member, the two first positioning members separate from the second positioning member and engage with the limiting structure.

5. The transporting system according to claim 4, wherein the second positioning member has an engaging slot at an end adjacent to the two first positioning members, the engaging slot being configured to receive the two first positioning members and to limit the two first positioning members from moving away from the body; wherein when the placing unit is inserted in the limiting slot and the two first positioning members and the limiting structure engage with each other, the placing unit is configured to be controlled by the horizontal moving assembly to move toward the limiting slot for guiding the two first positioning members moving toward each other by the limiting structure, such that the two first positioning members are received in the engaging slot.

6. The transporting system according to claim 5, wherein the placing unit further comprises a second elastic member disposed on the body, an end of the second elastic member being fixed on the body, the other end of the elastic member abutting the second positioning member; wherein when the two first positioning members are received in the engaging slot, the second elastic member is compressed and allows a portion of the second positioning member to abut a portion of each of the two first positioning members.

7. The transporting system according to claim 2, wherein the placing assembly further comprises a buffering unit having an end connected to the horizontal moving assembly, the other end of the buffering unit being connected to the body, and the body being configured to swing upwardly or downwardly relative to the buffering unit within a predetermined range.

8. The transporting system according to claim 1, wherein the storage device comprises a plurality of rotation plates stacked on each other and spaced apart from each other, and the rotation plates are configured to rotate around a same axis.

9. The transporting system according to claim 1, comprising a plurality of storage devices each having a plurality of rotation plates stacked on each other and spaced apart from each other, the rotation plates being controlled to rotate around a same axis, the storage devices being configured to be controlled and rotate or move relative to each other.

* * * * *